United States Patent [19]
Kim et al.

[11] Patent Number: 6,160,130
[45] Date of Patent: Dec. 12, 2000

[54] PREPARATION OF ALKYLENE CARBONATE USING MANGANESE HALIDES AS CATALYST

[75] Inventors: Hoon Sik Kim, Seoul; Jai Jun Kim, Kyunggido; Byung Gwon Lee; Young Soo Kwon, both of Seoul, all of Rep. of Korea

[73] Assignee: Korea Institute of Science and Technology, Seoul, Rep. of Korea

[21] Appl. No.: 09/477,828

[22] Filed: Jan. 5, 2000

[30] Foreign Application Priority Data

Jul. 26, 1999 [KR] Rep. of Korea ............ 99-30400

[51] Int. Cl.$^7$ ................................ C07D 317/08

[52] U.S. Cl. ............................ 549/230; 549/228
[58] Field of Search ................... 549/230, 228

*Primary Examiner*—Amelia Owens
*Attorney, Agent, or Firm*—Arent Fox Kintner Plotkin & Kahn, PLLC

[57] ABSTRACT

The present invention relates to a method for preparing alkylene carbonate by reacting alkylene oxide with carbon dioxide in the presence of a catalyst comprising:
a) at least one alkali metal halide selected from the group consisting of MCl, MBr and MI, whrerin M is alkali metal; and
b) at least one manganese halide selected from the group consisting of $MnCl_2$, $MnBr_2$ and $MnI_2$.

12 Claims, No Drawings

PREPARATION OF ALKYLENE CARBONATE USING MANGANESE HALIDES AS CATALYST

BACKGROUND OF THE INVENTION

1. Field of the Invention

The present invention relates to a method for preparing alkylene carbonate by reacting alkylene oxide with carbon dioxide. More particularly, the present invention relates to a method for preparing alkylene carbonate by reacting alkylene oxide with carbon dioxide in the presence of a catalyst system comprising MX and $MnY_2$ (M: alkali metal, X, Y: halide)

2. Description of the Prior Art

Alkylene carbonates are used in polycarbonate synthesis, as an intermediate in pharmaceutical processes, an oxyalkylation agent in dyestuff syntheses and a solvent in textile production processes. Conventionally, alkylene carbonate has been produced by reacting alkylene oxide with carbon dioxide in the presence of a catalyst, as shown in scheme 1.

Scheme 1

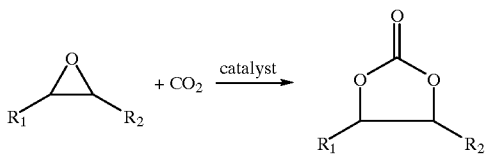

There are substantial literatures in the art with respect to the catalytic reaction of the alkylene oxide and carbon dioxide. Numerous catalysts have been proposed including alkali or alkali earth metal halide, ammonium halide and phosphonium halides.

For example, U.S. Pat. No. 4,881,555, U.S. Pat. No. 4,931,571 and Japanese Laid-Open Patent No. 7-206846 teaches a process for preparing an alkylene carbonate that employs a catalyst selected from the group consisting of organic quaternary ammonium halide, organic quaternary phosphonium halide, organic sulfonium halides and organic antimony halides. Japanese Laid-Open Patent No. 9-067365 discloses a method for preparing an alkylene carbonate wherein a catalyst comprising an alkali or alkali earth metal halide is used. Japanese Laid-Open Patent No. 8-059557 also discloses an alkali halide catalyst.

U.S. Pat. No. 2,773,070 introduces as a catalyst an ion exchange resin containing quaternary phosphonium halide groups, and U.S. Pat. No. 4,233,221 discloses DOWEX and Amberlite ion exchange resin. It was found that the anion-exchange resin catalysts lose their catalytic activity over a period of use.

U.S. Pat. No. 4,665,467 and U.S. Pat. No. 5,283,356 disclose methods for preparing alkylene carbonate by using a phthalocyanine or a porphyrine catalyst containing Co, Cr, Fe, Mn, Ni, Ti, V and Zr. In addition, JP 7-206847 discloses a process for preparing alkylene carbonate by using a rubidium or cesium substituted heteropoly acid catalyst.

In order to provide an attractive process for preparing alkylene carbonate, the process should achieve high selectivity to alkylene carbonate and should be economical. However, the processes disclosed in the above literatures has one or more problems in terms of yield, reaction condition, cost, etc.

SUMMARY OF THE INVENTION

An object of the present invention is to provide a method of producing alkylene carbonate with a high yield in a short reaction time under mild reaction conditions. More particularly, the object of the present invention is to provide a method of producing alkylene carbonate under milder reaction condition by using a new catalyst system comprising MX and $MnY_2$ (M: alkali metal, X, Y: halide).

DETAILED DESCRIPTION OF THE INVENTION

The present invention is directed to a new method of preparing alkylene carbonate by reacting alkylene oxide with carbon dioxide, which obviates above mentioned prior art's problem.

The present invention provides a new method of preparing alkylene carbonate by reacting alkylene oxide with carbon dioxide in the presence of a catalyst system comprising a) at least one alkali metal halide selected form the group consisting of MCl, MBr and MI, wherein M is alkali metal and b) at least one manganese halide selected form the group consisting of $MnCl_2$, $MnBr_2$ and $MnI_2$.

The present inventors have found that the above mentioned catalyst system is more effective than the conventional catalyst system in preparing alkylene carbonate of the formula

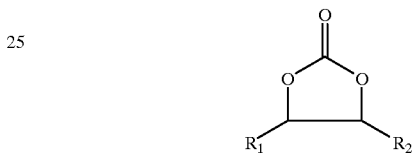

wherein $R_1$ and $R_2$ are independently hydrogen or $C_1\sim C_4$ alkyl group.

Manganese halides ($MnY_2$) used in the present invention include $MnCl_2$, $MnBr_2$ and $MnI_2$ and the alkali metal halides (MX) include NaCl, NaBr, NaI, KCl, KBr, KI, RbCl, RbBr, RbI, CsCl, CsBr, CsI. Preferable alkali metal is Na or K.

It is preferable to include at least one Br or I in manganese halides and alkali metal halides. In composing a catalyst system expressed as $a[MX]/b[MnY_2]$, the ratio of a to b is preferably a:b=20:1~1:5.

The amount of catalyst is preferably 0.001–5 mol % of the alkylene oxide.

Since the reaction is not greatly influenced by nitrogen, hydrogen, hydrocarbons and water typically present in carbon dioxide and alkylene oxide, it is possible to use commercially available carbon dioxide and alkylene oxide without a purification step.

Considering the equipment and operating cost, it is preferable to operate a reaction at a pressure of 5~100 atm, and a temperature of 80~170° C. When the reaction temperature is too high, alkylene carbonate undergoes self-polymerization reaction.

Although the above reaction can be performed in the absence of a solvent, it is possible to use a solvent to prevent excessive heat production during the reaction. As a solvent, alkylene carbonate identical with the one to be produced from the reaction is preferable. Thus, ethylene carbonate is a preferable solvent when ethylene carbonate is synthesized from ethylene oxide, and propylene carbonate is preferable when propylene carbonate is synthesized from propylene oxide. Alkylene carbonate different from the one to be produced from the reaction can be also used as a solvent. For example, propylene carbonate can be used as a solvent in the synthesis of ethylene carbonate (see Examples 36~39).

The reaction could be performed by a batch process using the reactor provided with a stirrer or by a continuous process using a bubble column.

EXAMPLES

The present invention will be further illustrated by the following examples, but, of course, should not construed as in any way limiting its scope.

Example 1

To a 200 ml high pressure reactor, ethylene oxide (16.80 g, 380 mmol), $MnBr_2$ (210 mg, 0.98 mmol) and KBr (238 mg, 1.97 mmol) were added and the reactor was pressurized to 10 atm with $CO_2$. The reactor was heated to 100° C., and then carbon dioxide was injected again to the pressure of 30 atm. During the reaction, carbon dioxide was continuously supplied to maintain the pressure of the reactor at 30 atm. After the reaction at 100° C. for 1 hour, the reactor was cooled to room temperature. Volatiles were removed and the solid product was isolated and weighed to be 31.6 g. The yield analyzed by gas-liquid chromatography was 94%.

The yield was calculated as follows:

$$\text{Yield of alkylene carbonate (\%)} = \frac{\text{Moles of alkylene carbonate produced}}{\text{Moles of alkylene oxide}} \times 100$$

Examples 2~12

The process of Example 1 was repeated except that different catalyst systems were employed in place of catalyst system comprising $MnBr_2$ and KBr. The results are shown in Table 1.

TABLE 1

| Example | Catalyst system | Product weight (g) | Yield (%) |
|---|---|---|---|
| 2 | $NaCl/MnCl_2$ | 5.7 | 17 |
| 3 | $NaBr/MnCl_2$ | 12.8 | 38 |
| 4 | $NaI/MnCl_2$ | 28.9 | 86 |
| 5 | $KCl/MnCl_2$ | 6.7 | 20 |
| 6 | $KBr/MnCl_2$ | 18.1 | 54 |
| 7 | $KI/MnCl_2$ | 32.9 | 98 |
| 8 | $KCl/MnBr_2$ | 21.8 | 65 |
| 9 | $KBr/MnBr_2$ | 31.6 | 94 |
| 10 | $KCl/MnI_2$ | 32.9 | 98 |
| 11 | $KBr/MnI_2$ | 33.2 | 99 |
| 12 | $KI/MnI_2$ | 33.2 | 99 |

Examples 13~18

The process of Example 1 was repeated except that the molar ratios of catalyst systems of alkali metal halide to manganese halide were in the range of 20:1~1:5. The results are shown in Table 2.

TABLE 2

| Example | Catalyst system | a:b | Product weight (g) | Yield (%) |
|---|---|---|---|---|
| 13 | $KBr/MnBr_2$ | 20:1 | 3.8 | 9.7 |
| 14 | $KBr/MnBr_2$ | 10:1 | 4.4 | 13 |
| 15 | $KBr/MnBr_2$ | 5:1 | 26.2 | 78 |
| 16 | $KBr/MnBr_2$ | 1:1 | 31.7 | 94.3 |
| 17 | $KBr/MnBr_2$ | 1:2 | 32.2 | 96 |
| 18 | $KBr/MnBr_2$ | 1:5 | 31.9 | 95 |

Examples 19~22

The process of Example 1 was repeated except that the reaction temperatures were in the range of 80~170° C. The results are shown in Table 3.

TABLE 3

| Example | Temperature (° C.) | Product weight (g) | Yield (%) |
|---|---|---|---|
| 19 | 80 | 11.8 | 35 |
| 20 | 90 | 21.8 | 65 |
| 21 | 120 | 32.6 | 97 |
| 22 | 170 | 30.6 | 91 |

Examples 23~25

The process of Example 1 was repeated except that the reaction pressures were in the range of 10~100 atm. The results are shown in Table 4.

TABLE 4

| Example | Pressure (atm) | Product weight (g) | Yield (%) |
|---|---|---|---|
| 23 | 10 | 30.6 | 91 |
| 24 | 50 | 32.6 | 97 |
| 25 | 100 | 32.6 | 97 |

Examples 26~30

The process of Example 1 was repeated except that the molar ratios of a catalyst mixture to the ethylene oxide were in the range of 0.001~5. The results are shown in Table 5.

TABLE 5

| Example | Catalyst mixture/ethylene oxide (mol %) | Product weight (g) | Yield (%) |
|---|---|---|---|
| 26 | 0.001 | 9.4 | 13 |
| 27 | 0.01 | 18.8 | 56 |
| 28 | 0.1 | 29.9 | 89 |
| 29 | 1 | 32.9 | 98 |
| 30 | 5 | 33.2 | 99 |

Examples 31~35

The process of Example 1 was repeated except that the different catalyst systems and/or alkylene oxides were employed. The results are shown in Table 6.

TABLE 6

| Example | Catalyst system | Alkylene oxide | Product weight (g) | Yield (%) |
|---|---|---|---|---|
| 31 | $KBr/MnBr_2$ | Propylene oxide | 35.3 | 91 |
| 32 | | 2-methyl-1,2-epoxypropane | 12.7 | 29 |
| 33 | $KI/MnBr_2$ | Ethylene oxide | 33.2 | 99 |
| 34 | | Propylene oxide | 36.1 | 93 |
| 35 | | 2-methyl-1,2-epoxypropane | 18.5 | 42 |

Examples 36~39

The process of Example 1 was repeated except that the different solvents and/or the different amounts thereof were employed. The results are shown in Table

TABLE 7

| Example | Solvent | Solvent/ethylene oxide (%) | Product weight (g) | Yield (%) |
|---|---|---|---|---|
| 36 | Ethylene carbonate | 50 | 32.6 | 98 |
| 37 | Propylene carbonate | 100 | 32.6 | 98 |
| 38 | Ethylene carbonate | 150 | 31.9 | 95 |
| 39 | Propylene carbonate | 200 | 29.2 | 89 |

Examples 40–42

The process of Example 1 was repeated except that the different catalyst systems comprising three metal halides were employed. The results are shown in Table 8

TABLE 8

| Example | Catalyst | Catalyst ratio | Product weight (g) | Yield (%) |
|---|---|---|---|---|
| 40 | KBr/MnI$_2$/MnBr$_2$ | 2:1:1 | 33.2 | 99 |
| 41 | KBr/KCl/MnBr$_2$ | 1:1:2 | 32.2 | 96 |
| 42 | KI/KBr/MnCl$_2$ | 1:1:2 | 33.2 | 99 |

According to the present invention, alkylene carbonate can be economically produced from alkylene oxide and carbon dioxide by using the catalyst system comprising a) lead halides, indium halides or their mixture and b) alkali metal halides.

What is claimed is:

1. A method for preparing alkylene carbonate by reacting alkylene oxide with carbon dioxide in the presence of a catalyst, characterized in that the catalyst comprises:
    a) at least one alkali metal halide selected from the group consisting of MCl, MBr and MI, wherein M is alkali metal; and
    b) at least one manganese halide selected from the group consisting of MnCl$_2$, MnBr$_2$ and MnI$_2$.

2. A method according to claim 1, wherein M is Na or K.

3. A method according to claim 1, wherein manganese halide is MnCl$_2$ or MnBr$_2$, and alkali metal halide is alkali metal chloride or alkali metal bromide.

4. A method according to claim 1, wherein the molar ratio of a)/b) is in the range of 20:1~1:5.

5. A method according to claim 1, wherein the amount of catalyst is in the range of 0.001~5 mol % based on the raw material alkylene oxide.

6. A method according to claim 1, wherein the reaction temperature is in the range of 90~170° C.

7. A method according to claim 1, wherein the reaction pressure is in the range of 10~100 atm.

8. A method according to claim 1, wherein the reaction is carried out without a solvent.

9. A method according to claim 1, wherein the reaction is carried out with a solvent.

10. A method according to claim 9, wherein the solvent is the same with the produced alkylene carbonate.

11. A method according to claim 9, wherein the solvent is ethylene carbonate or propylene carbonate.

12. A method according to claim 1, wherein the alkylene carbonate produced has the following formula:

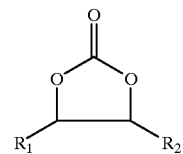

wherein R$_1$ and R$_2$ are independently hydrogen or C$_1$~C$_4$ alkyl group.

* * * * *